(12) United States Patent
Miller et al.

(10) Patent No.: US 8,513,466 B2
(45) Date of Patent: Aug. 20, 2013

(54) CLASS OF SOLUBLE, PHOTOOXIDATIVELY RESISTANT ACENE DERIVATIVES

(75) Inventors: Glen P. Miller, Lee, NH (US); Irvinder Kaur, Durham, NH (US)

(73) Assignee: University of New Hampshire, Durham, NH (US)

( * ) Notice: Subject to any disclaimer, the term of this patent is extended or adjusted under 35 U.S.C. 154(b) by 716 days.

(21) Appl. No.: 12/627,792

(22) Filed: Nov. 30, 2009

(65) Prior Publication Data

US 2011/0130594 A1 Jun. 2, 2011

(51) Int. Cl.
*C07C 323/31* (2006.01)

(52) U.S. Cl.
USPC .................................. 568/48; 568/34; 568/57

(58) Field of Classification Search
USPC ..................... 568/57, 660, 34, 42, 48; 257/40
See application file for complete search history.

(56) References Cited

U.S. PATENT DOCUMENTS

| | | | |
|---|---|---|---|
| 2,583,975 | A | 1/1952 | Tawney |
| 5,347,144 | A | 9/1994 | Garnier |
| 6,165,383 | A | 12/2000 | Chou |
| 6,265,243 | B1 | 7/2001 | Katz |
| H2084 | H | 10/2003 | Picciolo et al. |
| 6,690,029 | B1 | 2/2004 | Anthony |
| 7,276,395 | B2 | 10/2007 | Gerlach |
| 7,319,153 | B2 | 1/2008 | Vogel |
| 7,495,251 | B2 | 2/2009 | Zhu |
| 2006/0273311 | A1 | 12/2006 | Ohe |
| 2007/0137520 | A1 | 6/2007 | Brown |
| 2008/0113215 | A1 | 5/2008 | Kathirgemanathan |
| 2008/0191199 | A1 | 8/2008 | Anemian |
| 2008/0197325 | A1 | 8/2008 | Leeming |
| 2009/0230387 | A1* | 9/2009 | Ohe et al. .................. 257/40 |

FOREIGN PATENT DOCUMENTS

| | | | |
|---|---|---|---|
| JP | 2000021571 A | | 1/2000 |
| JP | 2006-199682 | * | 8/2006 |

OTHER PUBLICATIONS

Li et al, Chemical Materials, 2007, 19, 418-423.*
Kobayashi et al, Organic Letters, 2006, vol. 8, No. 11, 2385-2388.*
Wakayama et al, Nano Letters, 2008, vol. 8, No. 10, 3273-3277.*
Rogers, J.A., et al., Proc. Nat. Acad. Sci., 2001, 98:4835-4840.
Daniel, J.H., et al., ECS Transcations, 2006, 3:229-236.
Tunnell, A.J., et al., Org. Electron, 2008, 9:507-514.
Ono, K., et al., Tetrahedron, 2007, 61:9699-9704.
Palayangoda, S.S., et al., J. Org. Chem., 2007, 72:6584-6587.
Etienne, A. and C. Beauvios, Compt. Rend., 1954, 239:64-66.
Benor, A., et al., Org. Electron, 2007, 8:749-758.
Koch, N., et al., Org. Electron, 2006, 7:537-545.
Anthony, J.E., et al., J. Amer. Chem. Soc. 2001, 123:9482-9483.
Kaur, I., et al., J. Amer. Chem. Soc. 2008, 130, 16274-16286.
Chien, S.-H.; Cheng, M.-F.; Lau, K.-C.; Li, W.-K., Phys. Chem A 2005, 109, 7509-7518.
Cheng, M.-F; Li, W.-K., Chem. Phys. Lett. 2003, 368, 630-638.
Schleyer, P. V. R.; Manoharan, M.; Jiao, H.; Stahl, F. Org. Letters 2001, 3, 3643-3646.
Peter Van Zant in Microchip Fabrication, Fourth Edition, McGraw-Hill, New York (2000).
Materials Research Society Symposium Proceedings v 558, Materials Research Society, Warrendale, PA,, USA, pp. 403-408 (2000).
Kaur et al., "Substituent Effects in Pertacenes: Gaining Control over HOMO-LUMO Gaps and Photoxidative Resistances," J Am Chem Soc 130(48), pp. 16274-16286, Nov. 12, 2008, Abstract; p. 16280-p. 16281; Figs 1, 6-7.
Kaur et al., "Exploiting Substituent Effects for the Synthesis of a Photooxidatively Resistant Heptacene Derivative," J Am Chem Soc 131(10), pp. 3424-3425, Feb. 25, 2009, p. 3424-p. 3425.

* cited by examiner

*Primary Examiner* — Johann R Richter
*Assistant Examiner* — Pancham Bakshi
(74) *Attorney, Agent, or Firm* — Kevin M. Farrell, Esq.; Robert L. Hover, Esq.; Pierce Atwood, LLP

(57) ABSTRACT

The present invention is directed towards a new class of semi-conducting acene derivatives. These compounds are all soluble species and they all possess superior resistance to photooxidation as compared to their counterparts that lack the substitution patterns disclosed herein.

20 Claims, 6 Drawing Sheets

CLASS OF SOLUBLE, PHOTOOXIDATIVELY RESISTANT ACENE DERIVATIVES

The authors acknowledge the National Science Foundation (Nanoscale Science & Engineering Center for High-rate Nanomanufacturing, NSF-0425826) for financial support of this work. The Federal Government has a nonexclusive, non-transferable, irrevocable license in this invention on behalf of the United States. [37 CFR 401.14(b)].

BACKGROUND OF INVENTION

Traditionally, inorganic materials have dominated the electronic device industry. For example, silicon arsenide and gallium arsenide have been used as semiconductor materials, silicon dioxide has been used as an insulator material, and metals such as aluminum and copper have been used as electrode materials. In recent years, however, there has been an increasing research effort aimed at using organic materials rather than the traditional inorganic materials in electronic devices. Among other benefits, the use of organic materials may enable lower cost manufacturing of electronic devices, may enable large area applications, and may enable the use of flexible circuit supports for display backplane and integrated circuits.

Thin-film organic electronics promise lightweight, flexible, inexpensive devices produced using high rate, low cost, solution based methods like spin coating or reel-to-reel processing with compliant substrates (Rogers, J. A., et al., Proc. Nat. Acad. Sci., 2001, 98:4835-4840; Daniel, J. H., et al., ECS Tranactions, 2006, 3:229-236). In a low cost manufacturing environment, process steps like thermal annealing of thin-films to improve charge carrier mobilities (Tunnell, A. J., et al., Org. Electron, 2008, 9:507-514) should occur in air. Thus, it is important that the chosen organic semiconductor possesses both good solubility and excellent stability in air at elevated temperatures.

A variety of organic semiconductor materials have been considered, the most common being fused aromatic ring compounds as exemplified by small molecules such as pentacene-containing compounds, tetracene-containing compounds, anthracene-containing compounds, bis(acenyl)acetylene compounds, and acene-thiophene compounds. Several polymeric materials have also been considered such as regioregular polythiophenes, which are exemplified by poly(3-alkylthiophene), and polymers having fused thiophene units or bis-thiophene units.

Due to the high charge carrier mobilities associated with its thin films, pentacene is one of the most widely utilized organic semiconductor compounds. However, its application in thin-film electronic devices is hindered by its poor solubility and its propensity to photo-oxidize (Ono, K., et al., Tetrahedron, 2007, 61:9699-9704; Palayangoda, S. S., et al., J. Org. Chem., 2007, 72:6584-6587; Etienne, A. and C. Beauvios, Compt. Rend., 1954, 239:64-66; Benor, A., et al., Org. Electron, 2007, 8:749-758; Koch, N., et al., Org. Electron, 2006, 7:537-545). Pentacene oxidation leads to diminished electronic device performance. Pentacene-6,13-dione forms upon photo-oxidation and has been implicated as a deep charge carrier trap that reduces charge carrier mobility (Koch, N., et al., Org. Electron, 2006, 7:537-545).

Therefore, what is needed in the art is a pentacene derivative that can be cast into a thin-film organic semiconductor material that possesses greater solubility and greater photo-oxidative resistance than either pentacene or any of its presently known derivative compounds.

SUMMARY OF INVENTION

The present invention relates to novel and non-obvious organic semiconductor materials, organic semiconductor thin films and uses thereof. Presented herein, are embodiments of the present invention including novel and non-obvious pentacene-derived compounds that show surprising and exceptional photo-oxidative resistance together with thin-film field effect mobilities. Also provided are exemplary uses and devices incorporating the organic semi-conductor materials of the present invention.

The present invention relates to a new class of semi-conducting acene derivatives (organic semiconductor material) with the general structures shown in FIG. 1. These compounds are all soluble species and they all possess superior resistance to photooxidation as compared to their counterparts that lack the substitution patterns shown.

Recently, a combination experimental and computational study for a series of pentacene derivatives revealed that HOMO-LUMO gaps and photo-oxidative resistances are strongly influenced by both steric and electronic substituent effects. In the present invention we have discovered that steric and electronic substituent effects can be synergistically combined using substituents of the type disclosed herein. For example, pentacene derivatives having 6,13-bis(phenethylthio) substituents (see, for example, FIG. 2, compounds 2 and 3) are dramatically longer-lived than TIPS-pentacene (6,13-bis(triisopropyl-silylethynyl)pentacene), widely reported as one of the most stable prior art pentacene derivatives. (See, e.g., Anthony, J. E., et al., J. Amer. Chem. Soc., 2001, 123:9482-9483).

With regards to the structures (FIG. 1), $R_1$ represents any group containing pi (or π) electrons that is capable of participating in π-π-stacking interactions with the central acene core. This would include, without limitation, carbonyl moieties, alkene moieties, alkyne moieties, diene moieties and aromatic moieties of all types. $R_2$ through $R_{11}$ represent any group chosen from the following list: hydrogen, alkyl (e.g., methyl, ethyl, propyl, isopropyl, n-butyl-, isobutyl, sec-butyl, t-butyl, etc.), aryl (e.g., phenyl and substituted phenyl groups including but not limited to o-dialkylphenyl), heteroaryl (e.g., thiophene and substituted thiophenes), nitrile, carbonyl, trifluoromethyl, halogen (e.g., F, Cl, Br, I), alkylthio (e.g., simple alkylthio groups including but not limited to decylthio as well as complex alkylthio groups including but not limited to phenethylthio), arylthio, alkynyl (e.g., simple alkynyl [$C_2H$] and substituted alkynyl including but not limited to phenylethynyl and trialkylsilylethynyl). The compounds of the present invention may include all of the corresponding acene derivatives including tetracenes, pentacenes, hexacenes, heptacenes, octacenes and nonacenes.

π-π-stacking interactions are desirable in the organic semiconductor thin film compounds and materials of the present invention. Thus, the compounds and materials of the present invention should have a stack structure although the present application is not limited thereto. It is known that crystalline thin-films of pentacene (i.e., without substituents) takes a herringbone structure. As compared with this herringbone structure, a stack structure in which benzene rings are stacked in a π-π fashion [crystal structure in which adjacent molecular planes are stacked with respect to each other (adjacent molecular planes have parallel overlapping portions)] can realize an interaction of a stronger conjugated plane and will improve electronic characteristics considerably.

DETAILED DESCRIPTION OF INVENTION

Compounds of the Present Invention

The compounds of the present invention relate to novel and non-obvious acene derivatives. Acenes or large acenes or oligoacenes or polyacenes are a class of organic compounds and polycyclic aromatic hydrocarbons made up of linearly fused benzene rings. Pentacene contains five linearly fused benzene rings. Although the structure of pentacene resembles that of other aromatic compounds like anthracene, its aromatic properties are poorly defined by those of skill in the art and; as such, pentacene and its derivatives are the subject of much research.

Figure 1:
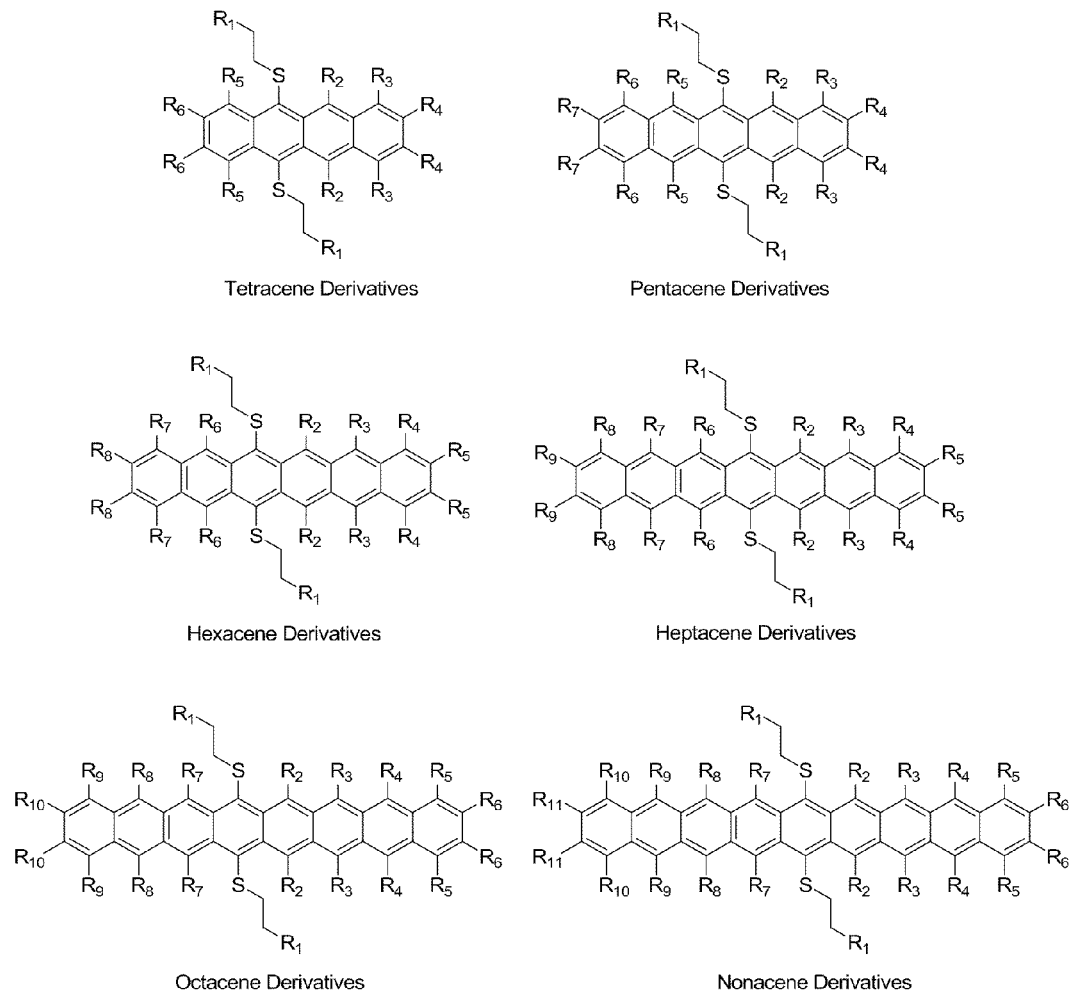
FIG. 1 shows a schematic representation of the generic compounds of the present invention.

The compounds of the present invention are acene derivatives bearing functional groups. FIG. 1 shows a schematic of the generic compounds of the present invention where $R_1$ is selected from, without limitation, carbonyl moieties, alkene moieties, alkyne moieties, diene moieties and aromatic moieties of all types. $R_2$ through $R_{11}$ represent any group chosen from the following list: hydrogen, alkyl (e.g., methyl, ethyl, propyl, isopropyl, n-butyl-, isobutyl, sec-butyl, t-butyl, etc.), aryl (e.g., phenyl and substituted phenyl groups including but not limited to o-dialkylphenyl), heteroaryl (e.g., thiophene and substituted thiophenes), nitrile, carbonyl, trifluoromethyl, halogen (e.g., F, Cl, Br, I), alkylthio (e.g., simple alkylthio groups including but limited to decylthio as well as complex alkylthio groups including but limited to phenethylthio), arylthio, alkynyl (e.g., simple alkynyl [$C_2H$] and substituted alkynyl including but not limited to phenylethynyl and trialkylsilylethynyl). The compounds of the present invention may include all of the corresponding acene derivatives including tetracenes, pentacenes, hexacenes, heptacenes, octacenes and nonacenes. Exemplary compounds are shown as formulas 2 and 3 in FIG. 2. In other embodiments, the compounds of the present invention may be based on tetracene, pentacene, hexacene, heptacene, octacene and nonacene derivatives having 4, 5, 6, 7, 8 or 9 linearly fused benzene rings, respectively. Longer acene compounds are also contemplated by the present invention. Representative methods of synthesis of the compounds of the present invention are given below in the Exemplification section of this paper.

6,13-Bis(phenethylthio)pentacene (2)

Figure 2:
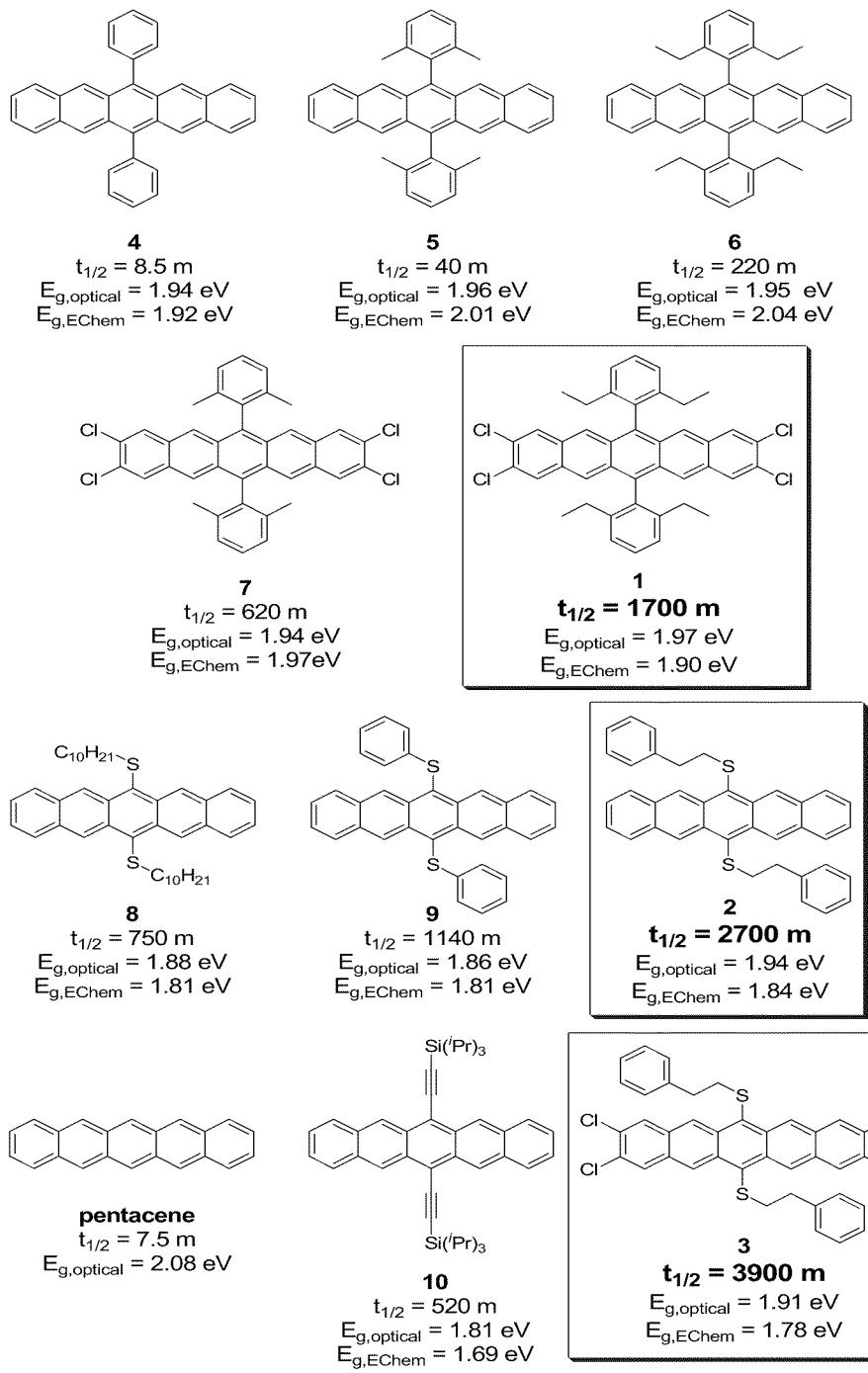
FIG. 2 shows Pentacene derivatives with half-lives under photo-oxidative conditions, optical HOMO-LUMO gaps and electrochemical HOMO-LUMO gaps. Half-life measurements for 1-10 were made using initial concentrations of $2.0 \times 10^{-4}$ M in $CH_2Cl_2$ with exposure to ambient light and air. For pentacene, a saturated solution in o-dichlorobenzene ($1.67 \times 10^{-7}$ M) was utilized.
Figure 3:
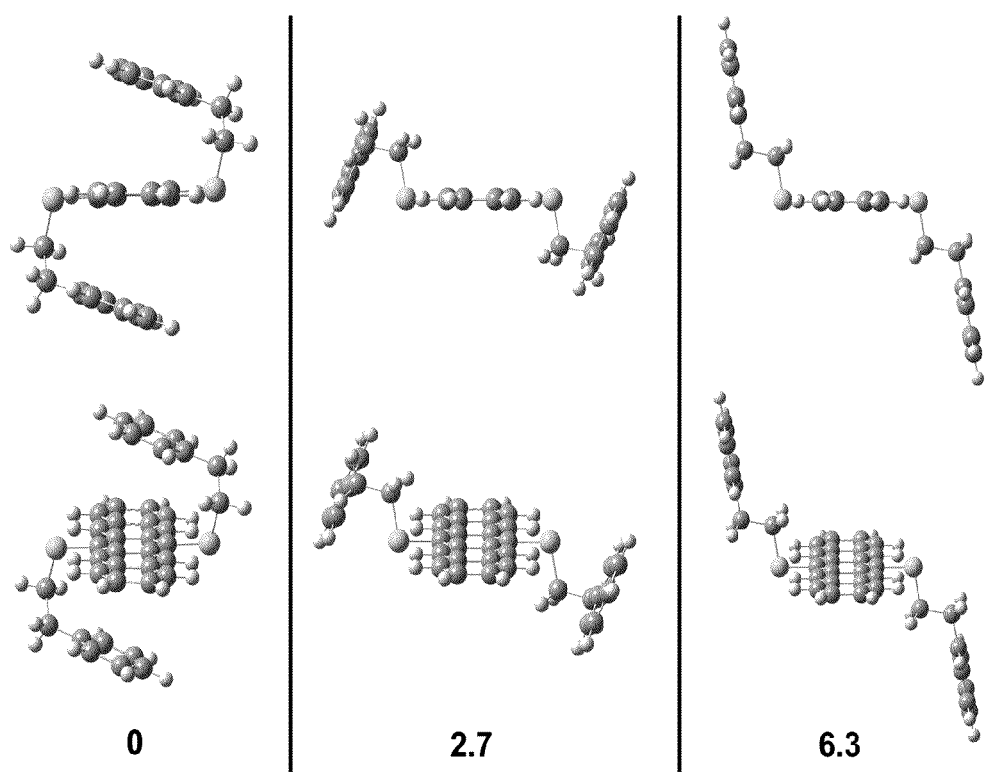
FIG. 3 shows calculated conformations for pentacene derivative 2 at the LMP2/6-311G*//B3LYP/6-31G* level following a Monte Carlo MMFF search with relative energies expressed in kcal/mol. The $\pi$-$\pi$-stacking conformation (left) represents the global minimum.

As illustrated as formula 2 in FIG. 2, the decylthio and phenylthio substituents at the 6,13 positions of 8 and 9 provide for enhanced photo-oxidative resistances compared to TIPS-pentacene [Kaur, I.; Jia, W.; Kopreski, R.; Selvarasah, S.; Dokmeci, M. R.; Pramanik, C.; McGruer, N. E. and Miller, G. P. J. Amer. Chem. Soc. 2008, 130, 16274-16286]. Because the decylthio and phenylthio groups are not constrained to lie over or under the π system as are the o-alkyl groups of 1 and 5-7, the enhanced photo-oxidative resistances are considered to be largely electronic effects, a conclusion corroborated by electrochemically determined HOMO and LUMO energies [Kaur, I.; Jia, W.; Kopreski, R.; Selvarasah, S.; Dokmeci, M. R.; Pramanik, C.; McGruer, N. E. and Miller, G. P. J. Amer. Chem. Soc. 2008, 130, 16274-16286]. The introduction of phenethylthio groups as in 2 is specifically designed to provide an enhanced steric component while leaving desirable electronic effects intact. Thus, the 3 atom S—C—C bridge between the pentacene skeleton and phenyl rings of 2 is the ideal length for enabling a low energy intramolecular π-π stacking conformation that effectively blocks the most reactive [(a) Chien, S.-H.; Cheng, M.-F; Lau, K.-C.; Li, W.-K. J. Phys. Chem. A 2005, 109, 7509-7518. (b) Cheng, M.-F.; Li, W.-K. Chem. Phys. Lett. 2003, 368, 630-638. (c) Schleyer, P. v. R.; Manoharan, M.; Jiao, H.; Stahl, F. Org. Letters 2001, 3, 3643-3646], center ring from participating in either Diels-Alder cycloadditions with $^1O_2$ or ET reactions with $^3O_2$. A Monte Carlo search (Monte Carlo search methods are defined herein and understood in the art as a class of computational algorithms that rely on repeated random sampling to compute their results, as is known to those of skill in the field) reveals that the π-π stacking conformation (FIG. 3, left) is the global minimum, corroborating its significance in the enhanced photo-oxidative resistance of 2. A second significant conformation of slightly higher energy utilizes CH-π interactions (FIG. 3, middle) for energy minimization. We expect both the π-π and CH-π motifs to be operating in crystalline thin-films. Crystal formation and structure determination studies are underway.

2,3,9,10-Tetrachloro-6,13-bis(phenethylthio)pentacene (3)

Derivative (formula) 3 as illustrated in FIG. 2 possesses an unmatched combination of steric and electronic substituent effects that maximally enhance its photo-oxidative resistance. Thus, 3 benefits from the unique electronic effects associated with 6,13 organothio substitution, the novel steric effect associated with π-π stacking 6,13 phenethylthio groups (FIG. 3), and the HOMO-LUMO energy lowering electronic effects of 2,3,9,10-tetrachloro substitution. With a half-life of 3900 minutes under photo-oxidative conditions, 3 is undeniably the most photo-oxidatively resistant pentacene derivative ever prepared. It is in fact 750% longer-lived than TIPS-pentacene, 10, under identical photo-oxidative conditions.

FET Studies of Thin-Films.

Figure 4:
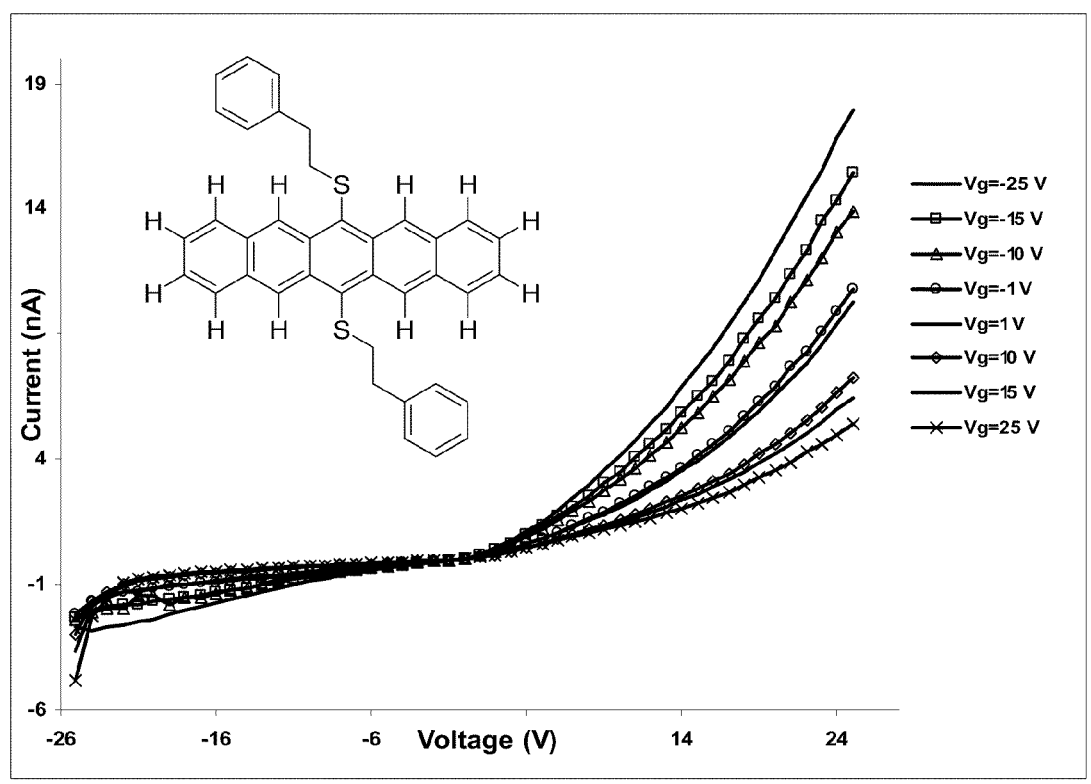
FIG. 4 shows gate-dependent Schottky barrier diode behavior of a thin film of 6,13-di(phenethylthio)pentacene suggesting photovoltaic (solar cells) applications for this derivative.
Figure 5A:
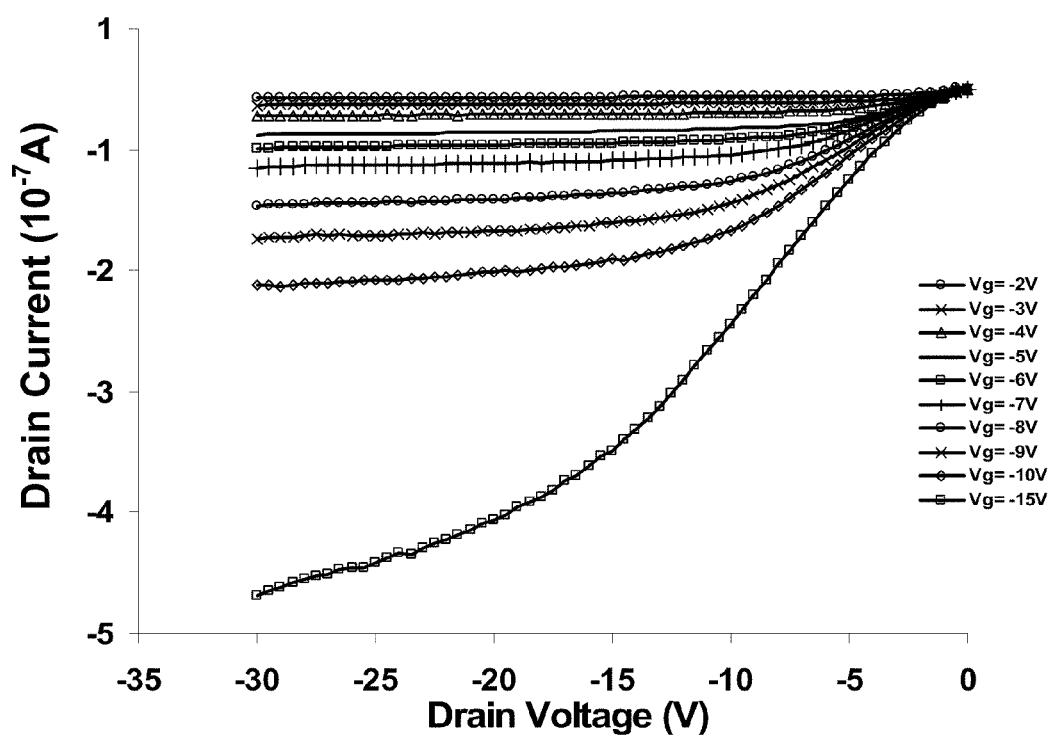
FIGS. 5 A & B shows the performance achieved for an organic thin-film transistor (OTFT) prepared from the pentacene derivative 2,3,9,10-tetrachloro-6,13-di(phenethylthio) pentacene. This device had a field-effect hole mobility of filed effect mobility of $2 \times 10^{-3}$ cm$^2$ V$^{-1}$ s$^{-1}$ and an on/off ration of $10^4$. A: Drain current versus drain-source voltage for several gate voltages. B: Bottom: Drain Current versus gate-source voltage. Upper Left: Chemical structure for 2,3,9,10-tetrachloro-6,13-di(phenethylthio)pentacene. Upper Right: Schematic cross section of a device with channel dimensions of W=2000 μm, L=10 μm.
Figure 5B:
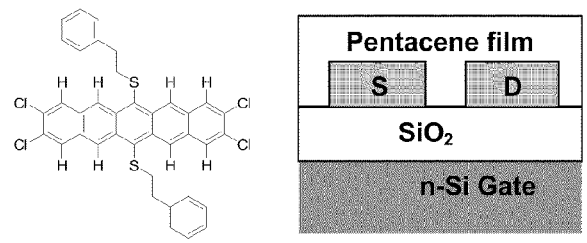
Figure 5B:
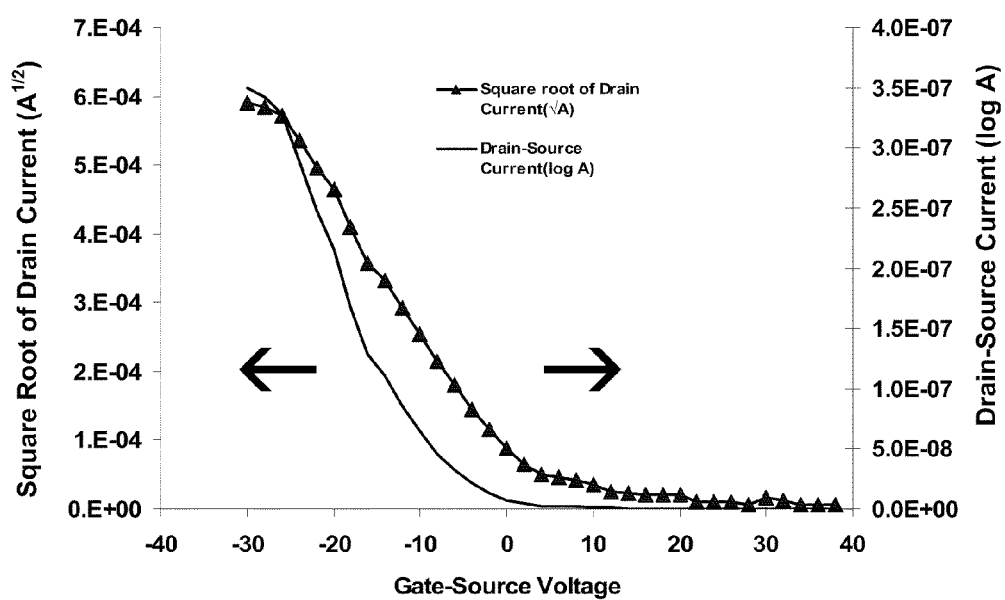

In addition to possessing superior photo-oxidative resistances, new pentacene derivatives 2-3 are soluble in a variety of organic solvents and therefore represent excellent candidates for organic thin-film electronic devices prepared using low cost manufacturing techniques. Spin-coating afforded thin films that exhibit either Schottky diode behavior (FIG. 4) or field effect mobility (FIGS. 5 A & B). The organic thin-film transistor (OTFT) prepared from pentacene derivative 3 showed a field effect mobility of $2 \times 10^{-3}$ cm$^2$ V$^{-1}$ s$^{-1}$ and an on/off ration of $10^4$. Given the enhanced photooxidative resistance of 2 and 3, these compounds represent a superior class for organic thin-film electronic devices.

Uses of the Present Invention

The acene derivatives disclosed herein are useful as organic semiconductor materials in semiconductor devices. Although there are numerous types of semiconductor devices, common to all is the presence of one or more semiconductor materials. Semiconductor devices include, for example, rectifiers, transistors (of which there are many types including p-n-p, n-p-n and thin-film transistors), light emitting semiconductors devices (for example, organic light emitting diodes), photoconductors, current limiters, thermistors, p-n junctions, field-effect diodes, Scottky diodes and other devices known in the art. In each semiconductor device, the semiconductor material is combined with one or more conductors or insulators to form the device. Semiconductor devices can be prepared or manufactured by known methods such as, for example, those described by Peter Van Zant in *Microchip Fabrication*, Fourth Edition, McGraw-Hill, New York (2000).

Electronic devices include components such as, e.g., transistors, arrays of transistors, diodes, capacitors, embedded capacitors and resistors that are used to form circuits. Electronic devices also include, for example, arrays of circuits that perform an electronic function. Examples of these arrays or integrated circuits are amplifiers, receivers, transmitters and oscillators.

Applications of these devices and arrays include, for example, radio frequency identification devices (RFIDs), smart cards, lamps, displays and the like. The present invention is not limited by the type of the device.

A particularly useful type of transistor device, e.g., the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes [see, for example, S. M. Sze, Physics of Semiconductor Devices, 2nd edition, John Wiley and Sons, page 492, New York (1981)]. These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), filled polymeric materials (for example, fiber-reinforced plastics (FRP)), and coated or uncoated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material or a polymeric dielectric layer.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

Alternatively, the gate dielectric may comprise an organic polymeric dielectric layer. A number of organic polymers have been considered as dielectric materials. These include polyimides, parylene C, crosslinked benzocyclobutene, and cyanoethylpullulan [see, for example, C. D. Sheraw et al., "Spin-on polymer gate dielectric for high performance organic thin film transistors", Materials Research Society Symposium Proceedings v 558, Materials Research Society, Warrendale, Pa., USA, pages 403-408 (2000); U.S. Pat. No. 6,265,243 (Katz); and U.S. Pat. No. 5,347,144 (Garnier)].

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

One particularly useful method of preparing thin film transistors or integrated circuits is by means of a flexible, repositionable polymeric aperture masks to create integrated circuits or integrated circuit elements. The techniques involve sequentially depositing material through a number of polymeric aperture masks formed with patterns that define layers, or portions of layers, of the circuit. In some embodiments, circuits can be created solely using aperture mask deposition techniques, without requiring any of the etching or photolithography steps typically used to form integrated circuit patterns. The techniques can be particularly useful in creating circuit elements for electronic displays such as liquid crystal displays and low-cost integrated circuits such as radio frequency identification (RFID) circuits. In addition, the techniques can be advantageous in the fabrication of integrated circuits incorporating organic semiconductors, which typically are not compatible with photolithography or other wet processes.

In various embodiments, different repositionable aperture masks such as flexible aperture masks, free-standing aperture masks and polymeric aperture masks formed with patterns may be used to define a layer or a portion of a layer of an integrated circuit. Repositionable polymeric aperture masks may have a thickness of approximately between 5 and 50 microns or approximately between 15 and 35 microns. The various deposition apertures in the aperture masks may have widths less than approximately 1000 microns, less than approximately 50 microns, less than approximately 20 microns, less than approximately 10 microns, or even less than approximately 5 microns. Apertures of these sizes are particularly useful in creating small circuit elements for integrated circuits. Moreover, one or more gaps between deposition apertures may be less than approximately 1000 microns, less than approximately 50 microns, less than approximately 20 microns or less than approximately 10 microns, which is also useful in creating small circuit elements. Also, aperture masks that include a pattern having a width greater than approximately 1 centimeter, 25 centimeters, 100 centimeters, or even 500 centimeters are also described. Patterns having these widths can be useful in creating various circuits over a larger surface area as described in greater detail below. In some embodiments, layer may be deposited on a substrate through repositionable polymeric aperture masks.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

The aperture masks can provide a number of advantages. For example, the aperture masks can facilitate the creation of relatively small circuit elements using deposition processes. The aperture masks can facilitate circuit elements having widths less than approximately 1000 microns, less than approximately 50 microns, less than approximately 20 microns, less than approximately 10 microns, or even less than approximately 5 microns. Also, the aperture masks can facilitate the creation of relatively large circuit patterns, in some cases having circuit elements of the relatively small widths mentioned above that cover large areas (such as 10 square centimeters, 50 square centimeters, 1 square meter, or even larger areas). In addition, the aperture masks can reduce costs associated with circuit fabrication, and in the case of organic semiconductors, can even improve device performance. Polymeric aperture masks can be created using a laser ablation process that may be faster and less expensive than other techniques. Also, inexpensive polymeric materials can allow the polymeric masks to be disposable, although reusable embodiments are also described.

In addition, polymeric material may be well suited to be impregnated with magnetic material. In that case, the magnetic material may be used to reduce sag in the mask as described below. Furthermore, polymeric material is often stretchable, which allows the mask to be stretched to either reduce sag or to align the mask.

The compounds of the invention can be used alone or in combination as the organic semiconductor layer of the OTFT (or other semiconductor device). The layer can be provided by any useful means, such as, for example, vapor deposition and printing techniques.

The compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The invention now being described, it will be apparent to one of ordinary skill in the art that many changes and modifications can be made thereto without departing from the spirit or scope of the invention.

As defined herein and as understood by those of ordinary skill in the art the art, HOMO and LUMO are acronyms for "Highest Occupied Molecular Orbital" and "Lowest Unoccupied Molecular Orbital," respectively. The difference of the energies of the HOMO and LUMO, termed the "HOMO-LUMO gap" for individual molecules and the "band gap" for collections of molecules in a thin-film can sometimes serve as a measure of the excitability of the molecule: the smaller the energy, the more easily it will be excited.

The HOMO level is to organic semiconductors and quantum dots what the valence band is to inorganic semiconductors. The same analogy exists between the LUMO level and the conduction band. The energy difference between the HOMO and LUMO level is approximately equal to the band gap energy.

When the molecule forms a dimer or an aggregate, the proximity of the orbitals of the different molecules induce a splitting of the HOMO and LUMO energy levels. This splitting produces vibrational sublevels which each have their own energy, slightly different from one another. There are as many vibrational sublevels as there are molecules that interact together. When there are enough molecules influencing each other (e.g., in an aggregate), there are so many sublevels that we no longer perceive their discrete nature: they form a continuum. We no longer consider energy levels, but energy bands. We no longer refer to the gap between filled and unfilled orbitals as the "HOMO-LUMO gap" but rather the "band gap".

EXEMPLIFICATION

General Remarks

2-Bromo-m-xylene, 2-bromo-1,3-diethylbenzene, phenyl-lithium (1.8 M solution in di-n-butyl ether), and n-butyl-lithium (2.5 M solution in hexanes) were purchased from Aldrich (St. Louis, Mo.). Thiophenol, 1-decanethiol, 4,5-dichlorobenzene-1,2-dicarboxylic acid, and triisopropylsilyl acetylene were purchased from TCI America (Portland, Oreg.). All purchased reactants and reagents were used without further purification. All reactions, unless otherwise noted, were carried out under the protection of $N_2$. All reaction containers were flame dried under vacuum before use. Solvents were purified by standard methods and dried if necessary. $^1$H NMR (500 MHz) spectra were recorded with a Varian AC 500 spectrometer. $^1$H and $^{13}$C NMR samples were internally referenced to TMS (0.00 ppm). Mass spectra were determined on LDI-TOF-MS (Shimadzu-Biotech) mass spectrometer.

Experimental Details of UV-Vis Spectroscopy

UV-visible spectra were obtained on Nikolet Evolution 300 spectrometer (in the range of 190-1100 nm) using 1 cm quartz cells. Dilute solutions (~$2.0 \times 10^{-4}$ M) of modified pentacenes (A-E) were prepared using degassed spectroscopic grade chloroform. The cells were protected from light until experiment began, at which point an initial spectrum was obtained. The solution was then exposed to ambient room light and air. The solutions were scanned for their UV-vis absorption at prescribed intervals until no absorbance in the visible region was recorded. Photooxidative stability of pentacenes was studied by monitoring change in their UV-vis absorption with time upon exposure to ambient light and air.

Experimental Details of Cyclic Voltammetry

Cyclic Voltammetry (CV) was performed with BAS-100B electrochemical analyzer in a three-electrode single-compartment cell with Ag/AgCl as the reference electrode, and tetrabutylammonium hexafluorophosphate $[Bu_4N]^+[PF_6]^-$ as the electrolyte. The solvent used is HPLC grade dichloromethane without any further purification. The scanning rate is 100 mV/sec and the concentration of $[Bu_4N]^+[PF_6]^-$ is 1.0 M. The concentration of pentacenes was 0.5 mM unless indicated otherwise.

6,13-Pentacenequinone

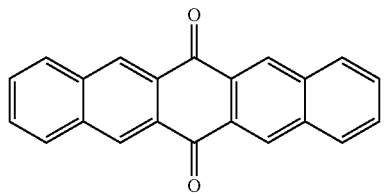 [SMILES: O=C1c2cc3ccccc3cc2C(=O)c2cc3ccccc3cc21]

To a clear solution of α,α,α',α'-tetrabromo-o-xylene (30.5 g, 0.073 mol) in DMF (100 mL) was added benzoquinone (3.125 g, 0.03 mol) and sodium iodide (27.25 g, 0.18 mol). The resulting brown suspension was heated and stirred at 120° C. overnight. After cooling to RT, the yellow solids were filtered via vacuum filtration. The yellow solids were washed with water, saturated sodium bisulfite solution and dried to yield the product (8.1 g, 91%). $^1$H NMR (500 MHz, CDCl$_3$): δ 8.96 (s, 4H), 8.14 (m, 4H), 7.72 (m, 4H). $^{13}$C NMR (125.68 MHz, CDCl$_3$): δ 183.2, 135.47, 130.80, 130.30, 129.98, 129.66. m/z: 308 [M$^+$].

trans-6,13-Dihydroxy-6,13-dihydropentacene

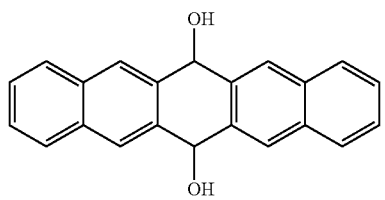 [SMILES: OC1c2cc3ccccc3cc2C(O)c2cc3ccccc3cc21]

To a suspension of 6,13-pentacenequinone (1.0 g, 3.24 mmol) in dry MeOH (40 mL) at 0° C. under an argon atmosphere was slowly added NaBH$_4$ (1.22 g, 32.46 mmol). The reaction mixture was stirred at 0° C. for 0.5 h and at RT for 1 h, and then quenched with H$_2$O at 0° C. The resulting mixture was filtered and washed with H$_2$O. The resulting solid was taken up in CHCl$_3$, then filtered and washed with CHCl$_3$, and dried in vacuo to give product as an off-white solid (0.92 g, 91%): mp 235° C. $^1$H NMR (500 MHz, DMSO-d$_6$): δ 8.12 (s, 4H), 7.95 (m, 4H), 7.48 (m, 4H), 6.63 (s, 2H), 5.81 (s, 2H). $^{13}$C NMR (125.68 MHz, DMSO-d$_6$): δ 138.19, 131.67, 127.47, 125.44, 120.91, 66.98. LDI-MS m/z: 312 [M$^+$], 296 [M$^+$-OH], 280 [M$^+$-2(OH)].

trans-6,13-Bis(phenethylethylthio)-6,13-dihydropentacene

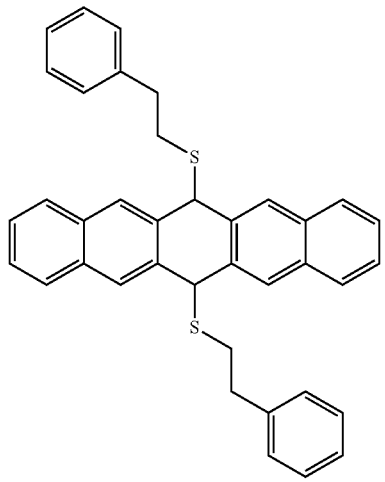

To a mixture of trans-6,13-dihydroxy-6,13-dihydropentacene (1.0 g, 3.20 mmol) and zinc iodide (1.02 g, 3.20 mmol) were added successively dry CH$_2$Cl$_2$ (100 mL) and phenethylthiophenol (0.77 g, 7.03 mmol) at RT under an argon atmosphere. The resulting mixture was stirred at RT for 2 h, and then quenched with H$_2$O. The mixture was extracted with CH$_2$Cl$_2$, and the organic layer was washed with brine and dried over anhyd. Na$_2$SO$_4$. After evaporation of solvents, the residue was purified by column chromatography on silica gel eluted with n-hexanes-CH$_2$Cl$_2$ (2:1) to give product as white solids in 71% yield (1.13 g). $^1$H NMR (500 MHz, CDCl$_3$): δ 7.80 (m, 4H), 7.70 (s, 4H), 7.46 (m, 4H), 7.29 (t, 4H, J=7.56 Hz), 7.20 (m, 6H), 5.24 (s, 2H), 2.90 (s, 8H). LDI-MS m/z: 552 [M$^+$], 416 [M$^+$-SCH$_2$CH$_2$C$_6$H$_5$], 280 [M$^+$-2(SCH$_2$CH$_2$C$_6$H$_5$)].

6,13-Bis(phenethylthio)pentacene

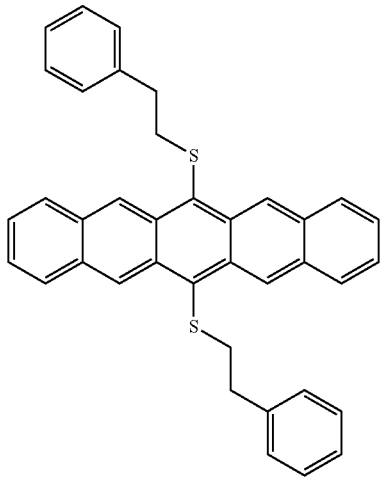 [SMILES: c1ccc(CCSc2c3cc4ccccc4cc3c(SCCc3ccccc3)c3cc4ccccc4cc23)cc1]

A mixture of trans-6,13-Bis(phenethylthio)-6,13-dihydropentacene (0.97 g, 1.76 mmol), tetrachloro-1,4-benzoquinone (0.87 g, 3.52 mmol) and potassium carbonate (2.43 g, 17.6 mmol) in dry benzene (170 mL) was stirred at 60° C. for 48 h under an argon atmosphere in the dark. After cooling to RT, the reaction mixture was filtered and washed with $CH_2Cl_2$. After evaporation of the filtrate, the solid residue was triturated with n-hexanes, filtered, and washed with hexane. After evaporation of the filtrate, the solid residue was passed through short column of n-$Al_2O_3$ eluted with $CH_2Cl_2$ and the deep blue band was collected. The solvent was evaporated to give pure 6,13-bis(phenethylthio)pentacene as deep blue solids in 72% yield (0.70 g). $^1$H NMR (500 MHz, $CDCl_3$): δ 9.63 (s, 4H), 8.00 (m, 4H), 7.40 (m, 4H), 7.19 (m, 6H), 7.06 (d, 4H, J=7.08 Hz), 3.32 (t, 4H, J=7.56 Hz), 2.86 (t, 4H, J=7.56 Hz). $^{13}$C NMR (125.68 MHz, $CDCl_3$): δ 140.91, 140.20, 132.83, 132.19, 128.88, 128.67, 128.52, 127.01, 126.49, 126.07, 38.97, 36.46. LDI-MS m/z: 550 [$M^+$], UV-vis $\lambda_{max}$(nm): 618, 571, 530.

4,5-Dichlorobenzene-1,2-dimethanol

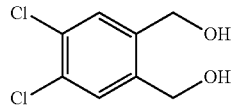 [SMILES: OCc1cc(Cl)c(Cl)cc1CO]

To a slurry of $LiAlH_4$ (1.61 g, 42.54 mmol) in dry THF (75 mL) cooled to −78° C., a solution of dimethyl 4,5-dichlorobenzene-1,2-dicarboxylic acid (5.0 g, 21.27 mmol) in dry THF (25 mL) was added dropwise over a period of 1 h. After slow warming of the system to RT over a period of 2 h the mixture was heated at reflux overnight. The heterogeneous mixture was then cooled to 0° C. and sodium hydroxide solution (15%, 100 mL) cooled to 0° C. was very slowly added. This was followed by addition of ice-cold water (100 mL), and the reaction mixture was diluted with diethyl ether (200 mL) and the organic layer was separated, dried over $MgSO_4$. Removal of solvents gave a white solid which was passed through a pad of silica gel to afford pure product in 88% yield (3.85 g). $^1$H NMR (500 MHz, $CDCl_3$): δ 7.60 (s, 2H), 4.65 (s, 4H), 4.50 (bs, 2H).

4,5-Dichlorobenzene-1,2-dicarbaldehyde

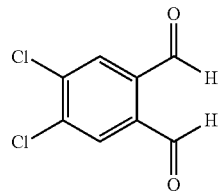 [SMILES: O=Cc1cc(Cl)c(Cl)cc1C=O]

To a dry 500 mL three-necked flask equipped with a thermometer and a dropping funnel, was added a solution of dry $CH_2Cl_2$ (60 mL) and oxalyl chloride (2.7 mL, 34.35 mmol) under Ar. The stirred solution was cooled to −78° C. and a solution of DMSO (4.24 mL, 59.67 mmol) in $CH_2Cl_2$ (10 mL) was added dropwise. The solution was stirred for 3-5 min. and 4,5-dichlorobenzene-1,2-dimethanol (2.0 g, 9.71 mmol) dissolved in $CH_2Cl_2$-DMSO mixture (25 mL) was added dropwise. The reaction was allowed to continue for 0.5 h and then triethylamine (24 mL, 0.18 mol) was slowly added at −78° C. the reaction mixture was allowed to stir for 10 min. and then slowly warmed to RT. Ice-cold water (50 mL) was added to the reaction mixture and the aqueous layer extracted with $CH_2Cl_2$ (2×50 mL) and then dried over $CaCl_2$. Removal of solvent gave the yellow solids of 4,5-dichlorobenzene-1,2-dicarbaldehyde in 78% yield (1.53 g). $^1$H NMR (500 MHz, $CDCl_3$): δ 10.46 (s, 2H), 8.05 (s, 2H). $^{13}$C NMR (125.68 MHz, $CDCl_3$): δ 189.92, 139.07, 135.32, 133.08.

2,3,9,10-Tetrachloro-6,13-pentacenequinone

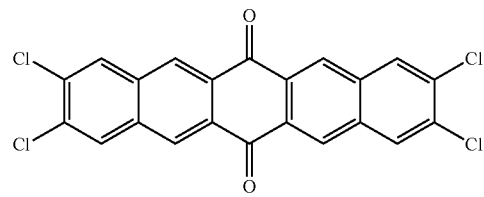 [SMILES: O=C1c2cc3cc(Cl)c(Cl)cc3cc2C(=O)c2cc3cc(Cl)c(Cl)cc3cc21]

4,5-Dichlorobenzene-1,2-dicarbaldehyde (2.0 g, 9.90 mmol) and 1,4-cyclohexanedione (0.62 g, 5.53 mmol) were stirred in 60 mL ethanol. To this was added dropwise with stirring, 10 mL of 5% aq potassium hydroxide. Upon addition of first drop, solution became black, brown, and then solids precipitate. Reaction mixture was stirred at RT for 1 h and refluxed for 2 h. Reaction mixture was cooled to RT, solids filtered, washed with water, dried to give 2,3,9,10-tetrachloro-6,13-pentacenequinone as brown solids in good yields (1.73 g, 70%). LDI-MS m/z: 446 [$M^+$].

trans-6,13-Dihydroxy-2,3,9,10-tetrachloro-6,13-dihyropentacene

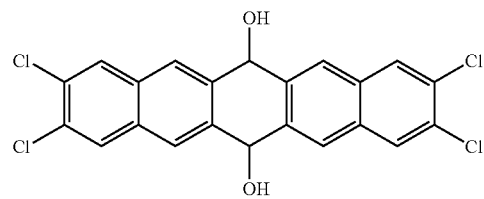 [SMILES: OC1c2cc3cc(Cl)c(Cl)cc3cc2C(O)c2cc3cc(Cl)c(Cl)cc3cc21]

To a suspension of 2,3,9,10-tetrachloro-6,13-pentacenequinone (1.0 g, 2.24 mmol) in dry MeOH (40 mL) at 0° C. under an argon atmosphere was slowly added $NaBH_4$ (0.85 g, 22.47 mmol). The reaction mixture was stirred at 0° C. for 0.5 h and at RT for 16 h, and then quenched with H2O at 0° C. The resulting mixture was filtered and washed with H2O and dried in vacuo to give product as a brown solids (0.92 g, 90%) which was identified as mixture of two isomers. $^1$H NMR (500 MHz, DMSO-d6): δ 8.36 (s, 4H), 8.16 (s, 4H), 6.82 (d, 2H), 5.82 (d, 2H). $^1$H NMR (500 MHz, DMSO-d6): δ 8.35 (s, 4H), 8.13 (s, 4H), 6.30 (d, 2H), 5.99 (d, 2H). LDI-MS m/z: 449.96[$M^+$], 431[$M^+$-OH], 415.97 [$M^+$-2(OH)].

2,3,9,10-Tetrachloro-trans-6,13-bis(phenethylthio)-6,13-dihydropentacene

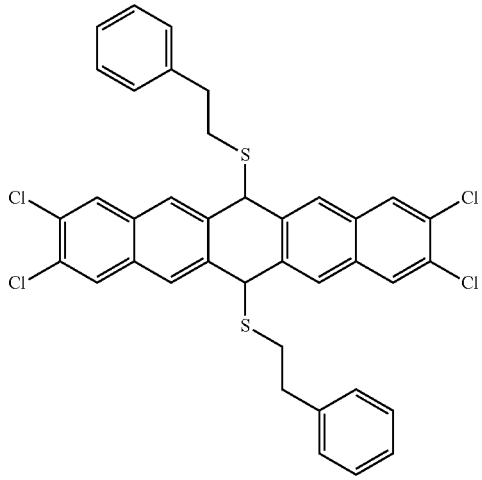 [SMILES: Clc1cc2cc3c(cc2cc1Cl)C(SCCc1ccccc1)c1cc2cc(Cl)c(Cl)cc2cc1C3SCCc1ccccc1]

To a mixture of trans-6,13-dihydroxy-2,3,9,10-tetrachloro-6,13-dihyropentacene (1.44 g, 3.20 mmol) and zinc iodide (1.02 g, 3.20 mmol) were added successively dry $CH_2Cl_2$ (100 mL) and phenethylthiophenol (0.97 g, 7.03 mmol) at RT under an argon atmosphere. The resulting mixture was stirred at RT for 2 h, and then quenched with $H_2O$. The mixture was extracted with $CH_2Cl_2$, and the organic layer was washed with brine and dried over anhyd. $Na_2SO_4$. After evaporation of solvents, the residue was purified by column chromatography on silica gel eluted with n-hexanes-$CH_2Cl_2$ (2:1) to give product as reddish brown solids in 68% yield (1.50 g). $^1$H NMR (500 MHz, $CDCl_3$): δ 7.80 (m, 4H), 7.57 (s, 4H), 7.26 (t, 4H, J=7.56 Hz), 7.17 (m, 6H), 5.21 (s, 2H), 2.88 (s, 8H). $^{13}$C NMR (125.68 MHz, $CDCl_3$): δ 140.51, 136.21, 131.51, 130.87, 128.81, 128.79, 128.58, 126.74, 126.50, 48.29, 36.15, 35.52.

2,3,9,10-Tetrachloro-6,13-bis(phenethylthio)pentacene

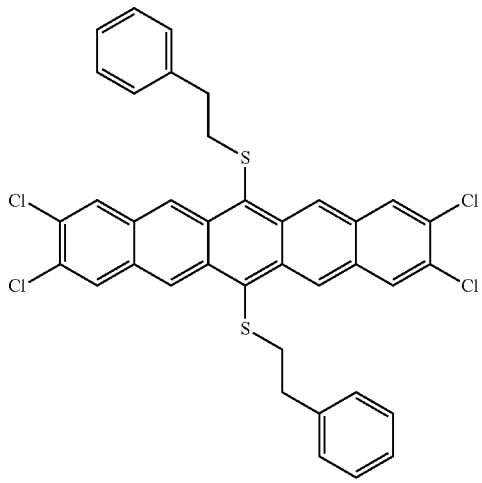 [SMILES: Clc1cc2cc3c(SCCc4ccccc4)c4cc5cc(Cl)c(Cl)cc5cc4c(SCCc4ccccc4)c3cc2cc1Cl]

A mixture of 2,3,9,10-tetrachloro-trans-6,13-bis(phenylethylthio)-6,13-dihydropentacene (0.3 g, 0.44 mmol), tetrachloro-1,4-benzoquinone (0.22 g, 0.89 mmol) and potassium carbonate (0.61 g, 4.45 mmol) in dry benzene (50 mL) was stirred at 60° C. for 48 h under an argon atmosphere in the dark. After cooling to RT, the reaction mixture was filtered and washed with $CH_2Cl_2$. After evaporation of the filtrate, the solid residue was passed through short column of n-$Al_2O_3$ eluted with $CH_2Cl_2$ and the deep blue band was collected. The solvent was evaporated to give pure 2,3,9,10-tetrachloro-6,13-bis(phenethylthio)pentacene as deep blue solids in 17% yield (0.05 g). $^1$H NMR (500 MHz, $CDCl_3$): δ 9.48 (s, 4H), 8.11 (s, 4H), 7.24 (m, 6H), 7.06 (m, 4H), 3.27 (t, 4H, J=7.32 Hz), 2.85 (t, 4H, J=7.32 Hz). $^{13}$C NMR (125.68 MHz, $CDCl_3$): δ 132.89, 132.44, 132.25, 128.95, 128.73, 128.59, 127.07, 126.56, 126.14, 38.04, 36.53. LDI-MS m/z: 688 [M$^+$], UV-vis $\lambda_{max}$(nm): 628, 577, 537.

What is claimed is:

1. A photooxidatively resistant acene composition selected from the group consisting of:

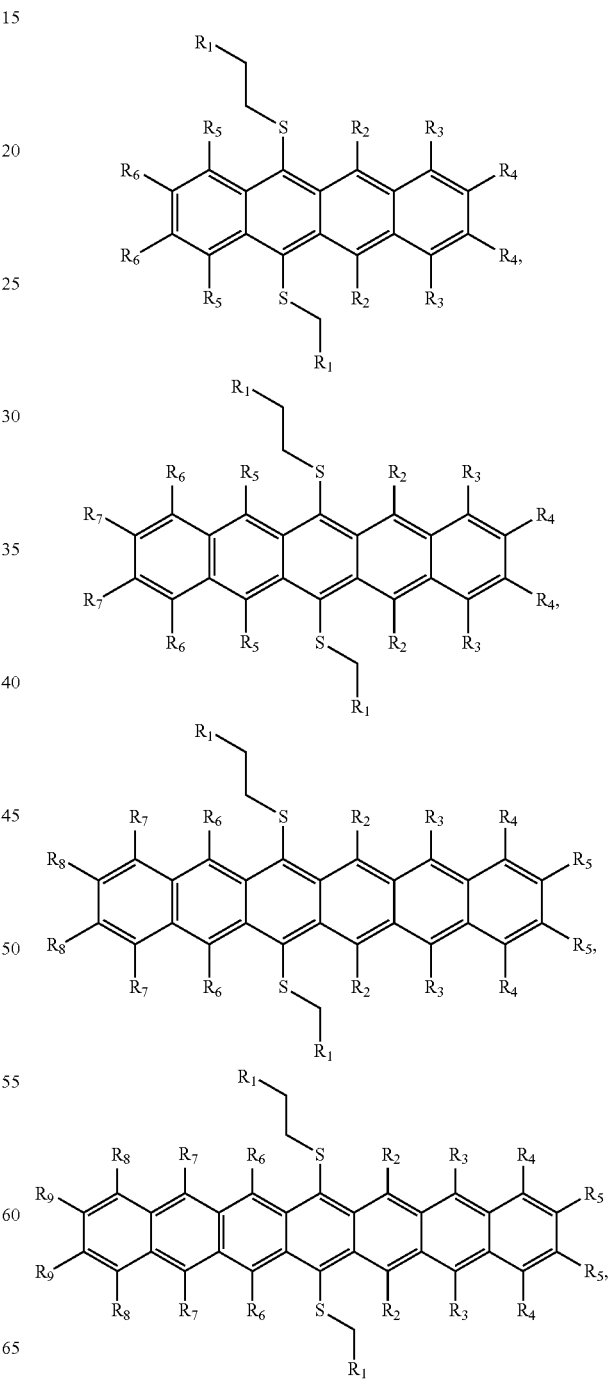

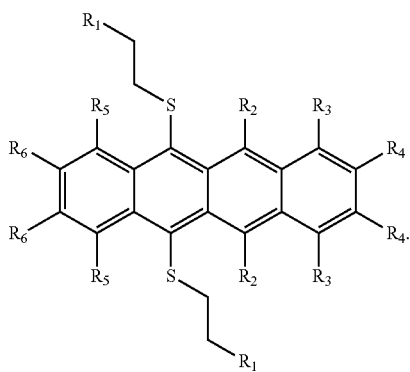

wherein $R_1$ is any group containing pi (or π) electrons that is capable of participating in ππ-stacking interactions with the central acene core and $R_2$ through $R_{11}$ represent any group chosen from the following list: hydrogen, alkyl, aryl, heteroaryl, nitrile, carbonyl, trifluoromethyl, halogen, alkylthio, arylthio, alkynyl.

2. The composition of claim 1, wherein said photooxidatively resistant acene is:

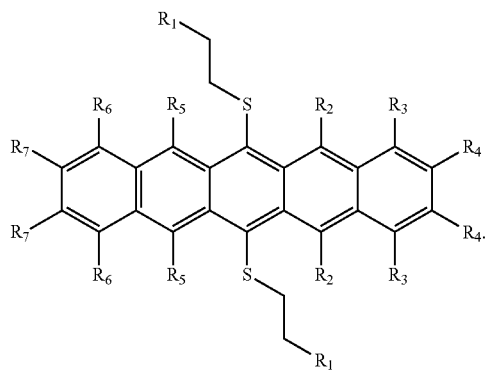

3. The composition of claim 1, wherein said photooxidatively resistant acene is:

4. The composition of claim 1, wherein said photooxidatively resistant acene is:

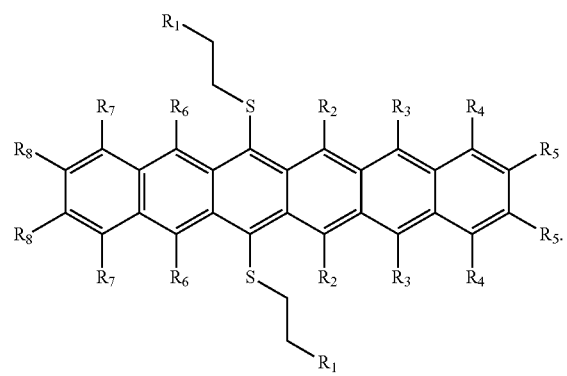

5. The composition of claim 1, wherein said photooxidatively resistant acene is:

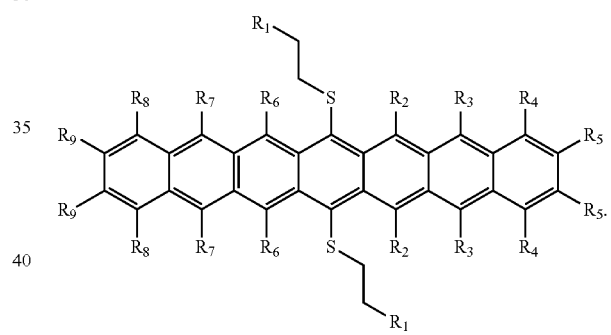

6. The composition of claim 1, wherein said photooxidatively resistant acene is:

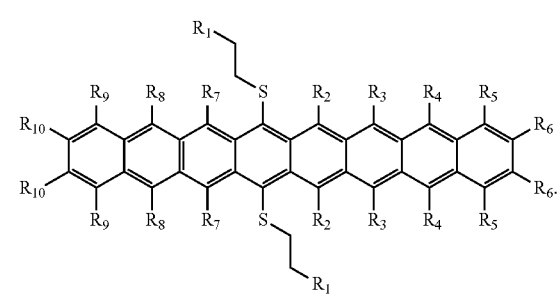

7. The composition of claim 1, wherein said photooxidatively resistant acene is:

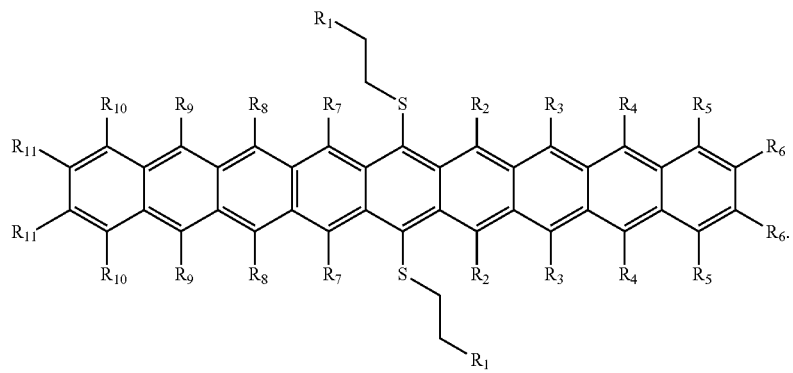

8. The composition of claim 1, wherein $R_1$ is selected from a group consisting carbonyl moieties, alkene moieties, alkyne moieties, diene moieties and aromatic moieties.

9. The composition of claim 1, wherein said photooxidatively resistant acene is:

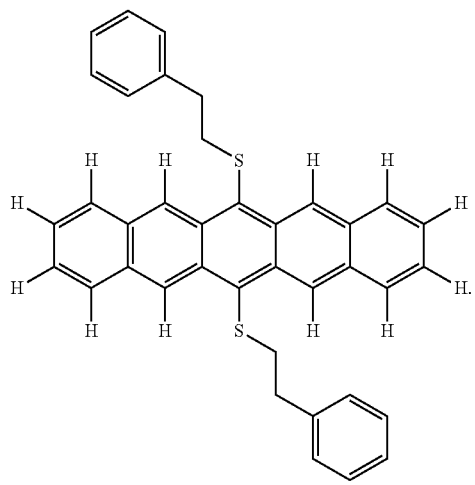

10. The composition of claim 1, wherein said photooxidatively resistant acene is:

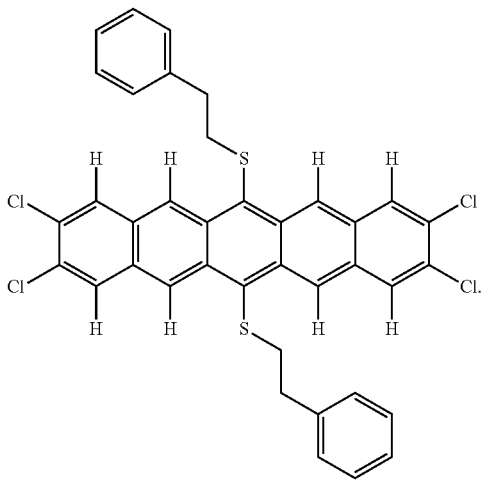 [SMILES: Clc1cc2cc3c(SCCc4ccccc4)c4cc5cc(Cl)c(Cl)cc5cc4c(SCCc4ccccc4)c3cc2cc1Cl]

11. An electronic device comprising an acene derivative selected from one or more of the group consisting of:

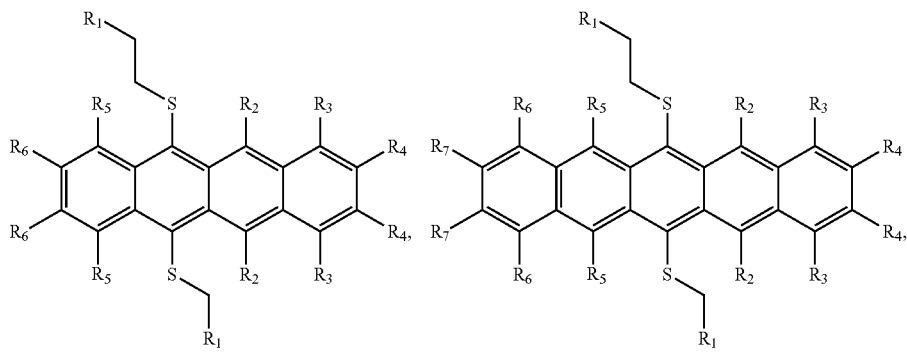

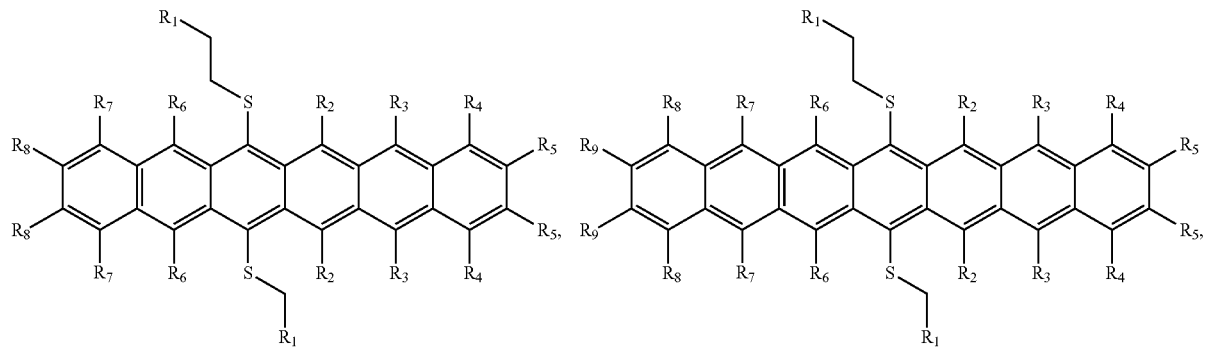

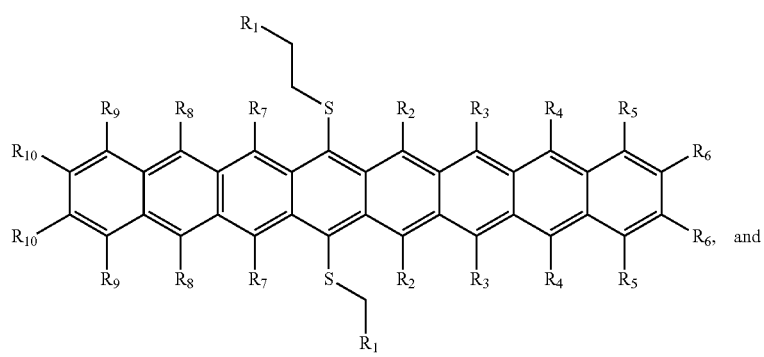

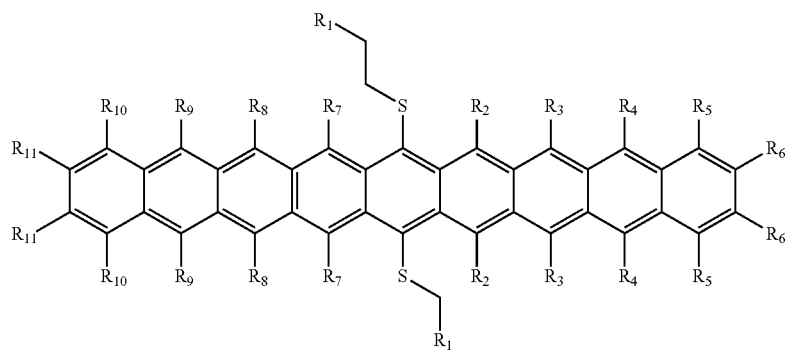

wherein $R_1$ is any group containing pi (or $\pi$) electrons that is capable of participating in $\pi\pi$-stacking interactions with the central acene core and $R_2$ through $R_{11}$ represent any group chosen from the following list: hydrogen, alkyl, aryl, heteroaryl, nitrile, carbonyl, trifluoromethyl, halogen, alkylthio, arylthio, alkynyl.

12. The acene derivative of the electronic device of claim 11, wherein $R_1$ is selected from a group consisting of carbonyl moieties, alkene moieties, alkyne moieties, diene moieties and aromatic moieties.

13. The composition of claim 11, wherein said photooxidatively resistant acene is:

14. The composition of claim 11, wherein said photooxidatively resistant acene is:

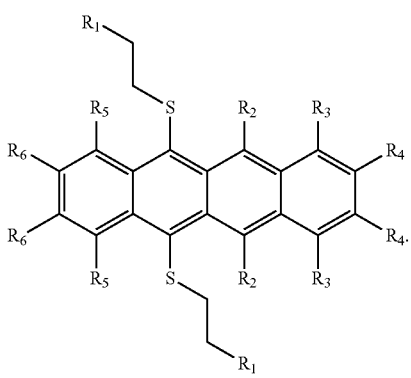

15. The composition of claim 11, wherein said photooxidatively resistant acene is:
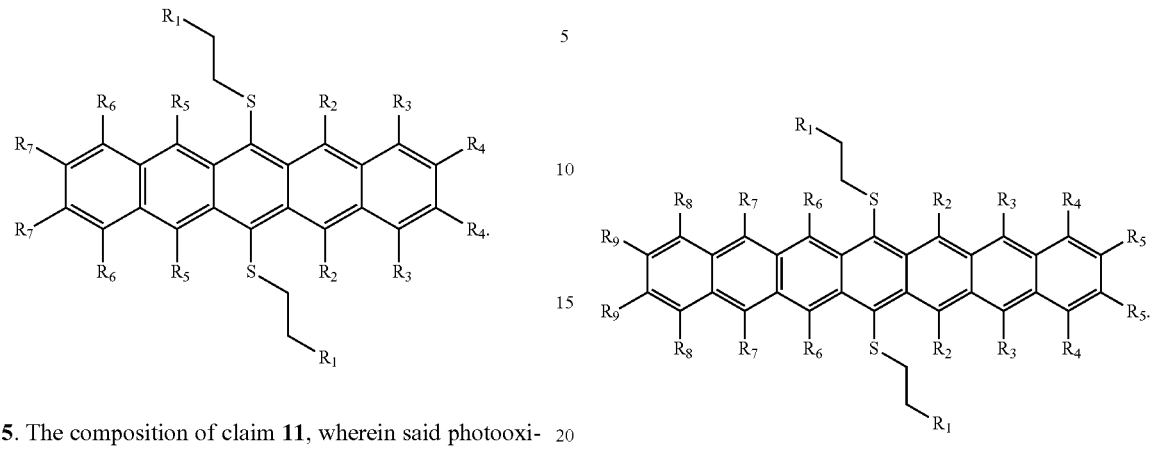
16. The composition of claim 11, wherein said photooxidatively resistant acene is:
17. The composition of claim 11, wherein said photooxidatively resistant acene is:
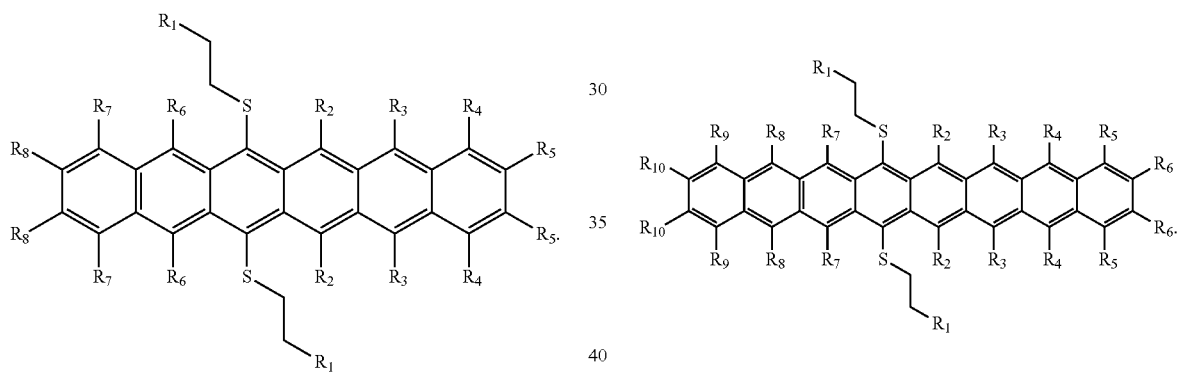
18. The composition of claim 11, wherein said photooxidatively resistant acene is:
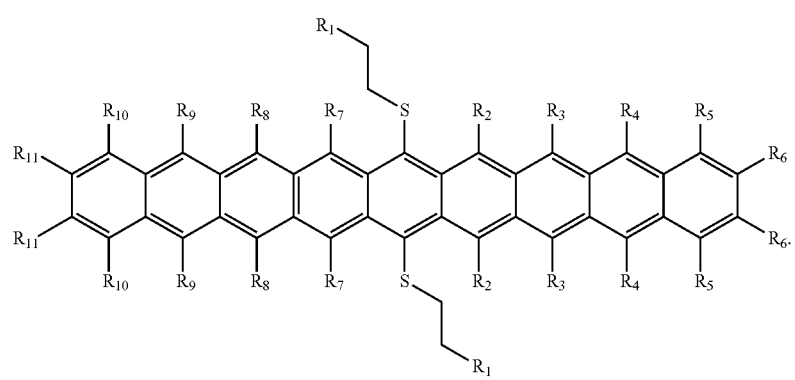

19. The photooxidatively resistant acene of the electronic device of claim 11, wherein the photooxidatively resistant acene has the structure
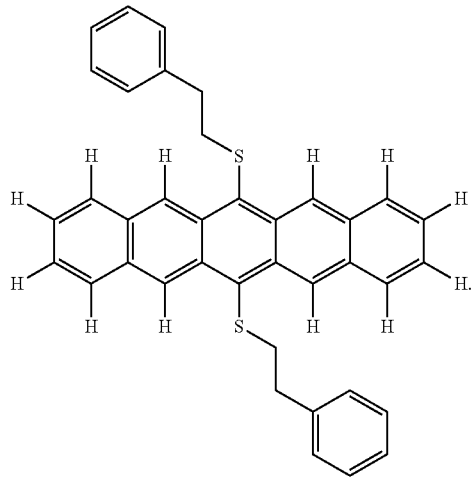
20. The photooxidatively resistant acene of the electronic device of claim 11, wherein the photooxidatively resistant acene has the structure:
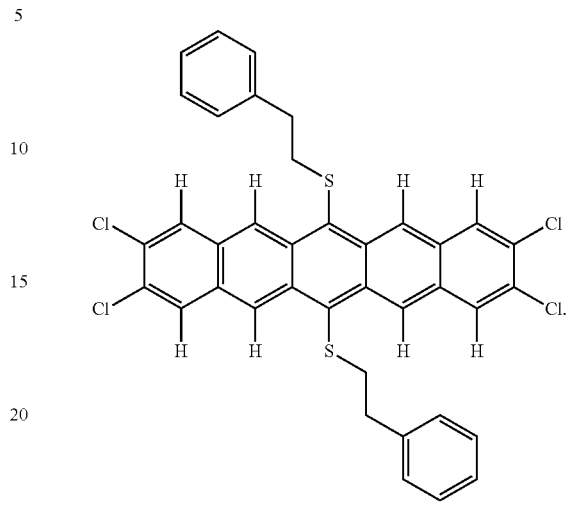
* * * * *

UNITED STATES PATENT AND TRADEMARK OFFICE
CERTIFICATE OF CORRECTION

PATENT NO. : 8,513,466 B2  
APPLICATION NO. : 12/627792  
DATED : August 20, 2013  
INVENTOR(S) : Glen P. Miller et al.

It is certified that error appears in the above-identified patent and that said Letters Patent is hereby corrected as shown below:

In the Claims

Please amend claims 1 & 11 as follows on the attached sheets:

Column 14 lines 11 - 20 should read

1. A photooxidatively resistant acene composition selected from the group consisting of:

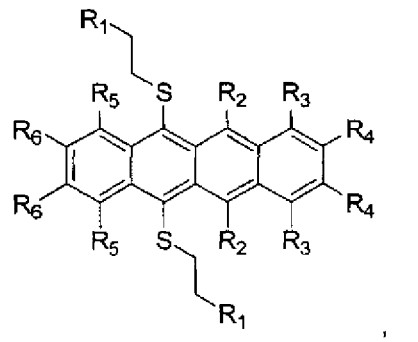

,

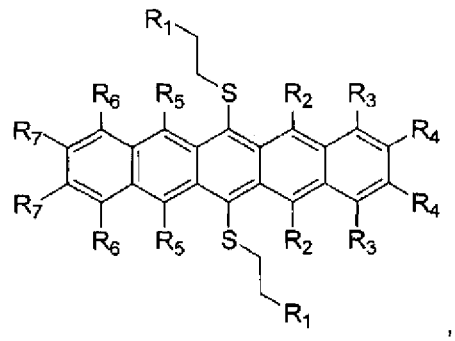

,

Signed and Sealed this  
Twenty-ninth Day of April, 2014

Michelle K. Lee  
*Deputy Director of the United States Patent and Trademark Office*

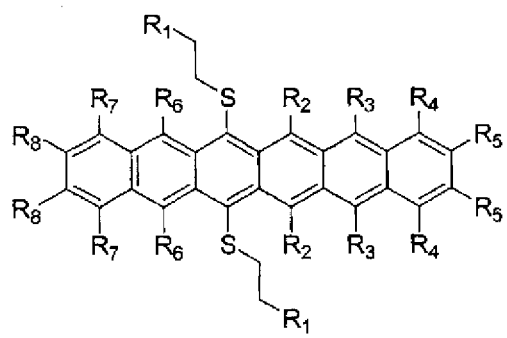
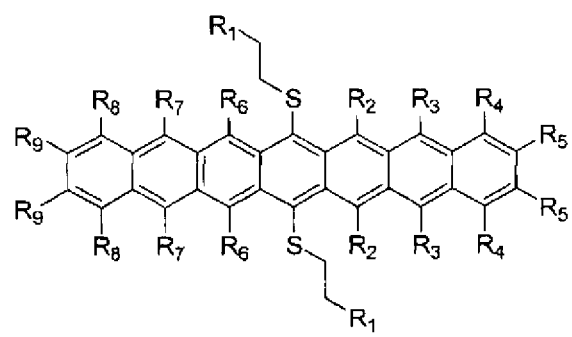
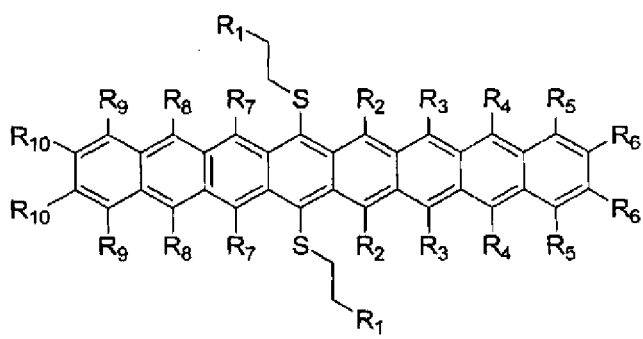
, and
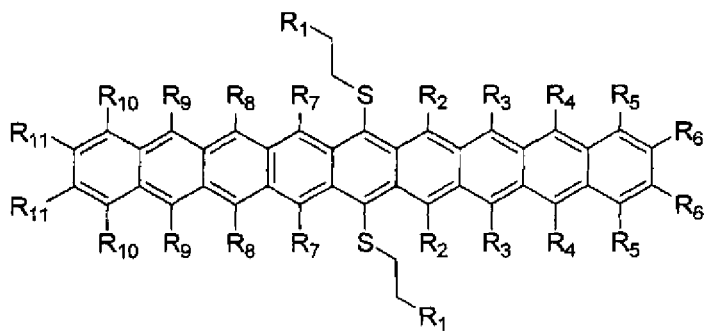
wherein $R_1$ is any group containing pi (or $\pi$) electrons that is capable of participating in $\pi$ $\pi$-stacking interactions with the central acene core and $R_2$ through $R_{11}$ represent any group chosen from the following list: hydrogen, alkyl, aryl, heteroaryl, nitrile, carbonyl, trifluoromethyl, halogen, alkylthio, arylthio, alkynyl.

CERTIFICATE OF CORRECTION (continued)
U.S. Pat. No. 8,513,466 B2

Column 18 lines 46 - 56 should read

11. An electronic device comprising an acene derivative selected from one or more of the group consisting of:

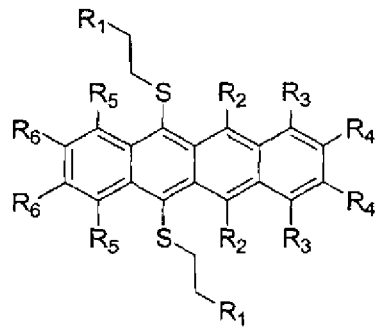

,

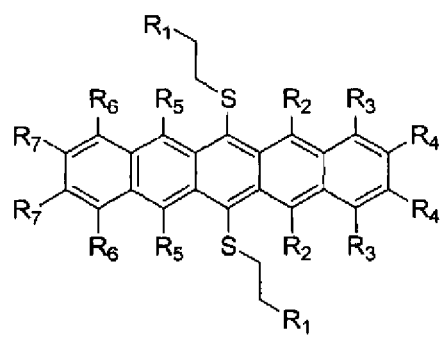

,

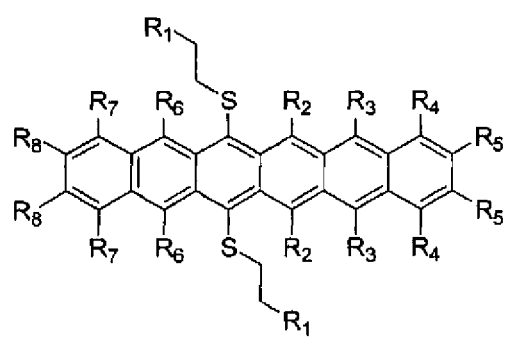

,

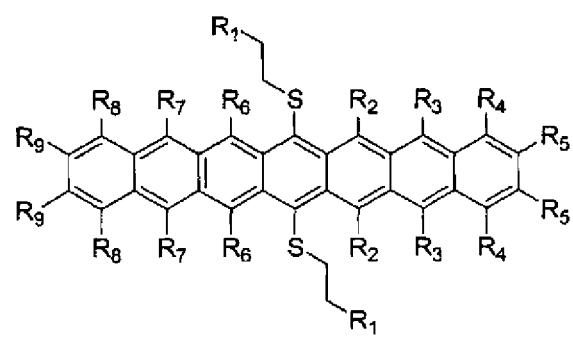

,

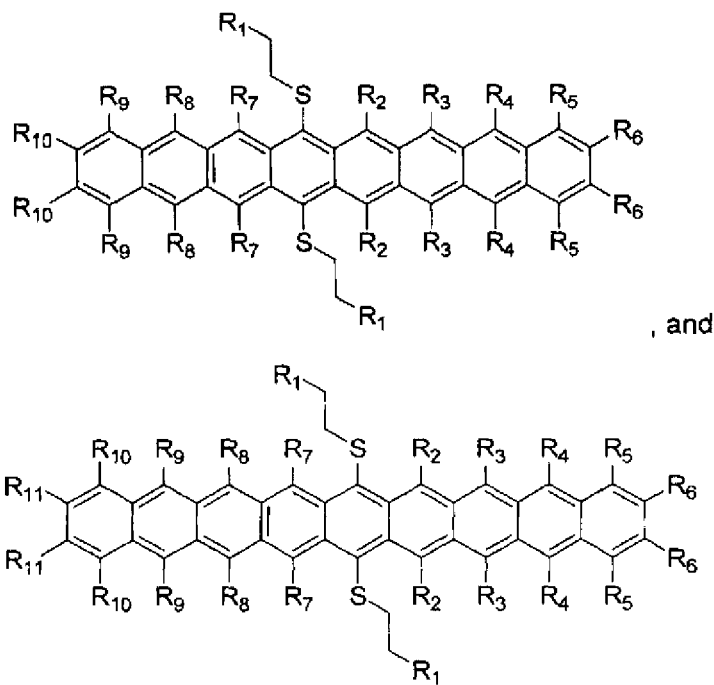
, and
wherein $R_1$ is any group containing pi (or $\pi$) electrons that is capable of participating in π π-stacking interactions with the central acene core and $R_2$ through $R_{11}$ represent any group chosen from the following list: hydrogen, alkyl, aryl, heteroaryl, nitrile, carbonyl, trifluoromethyl, halogen, alkylthio, arylthio, alkynyl.